United States Patent
Schena et al.

(10) Patent No.: US 9,452,019 B2
(45) Date of Patent: Sep. 27, 2016

(54) INSTRUMENT CARRIAGE ASSEMBLY FOR SURGICAL SYSTEM

(71) Applicant: Intuitive Surgical Operations, Inc., Sunnyvale, CA (US)

(72) Inventors: Bruce Michael Schena, Menlo Park, CA (US); Gregory W. Dachs, II, San Francisco, CA (US); Todd Solomon, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 460 days.

(21) Appl. No.: 13/907,049

(22) Filed: May 31, 2013

(65) Prior Publication Data

US 2013/0325034 A1 Dec. 5, 2013

Related U.S. Application Data

(60) Provisional application No. 61/654,391, filed on Jun. 1, 2012.

(51) Int. Cl.
*A61B 19/00* (2006.01)
*A61B 17/00* (2006.01)

(52) U.S. Cl.
CPC .......... *A61B 19/2203* (2013.01); *A61B 34/30* (2016.02); *A61B 34/37* (2016.02); *A61B 90/98* (2016.02); *A61B 2017/00477* (2013.01); *A61B 2034/2059* (2016.02)

(58) Field of Classification Search
CPC ................................. A61B 19/2203
See application file for complete search history.

(56) References Cited

U.S. PATENT DOCUMENTS

| | | | |
|---|---|---|---|
| 2005/0115352 A1 | 6/2005 | Tanaka | |
| 2007/0119274 A1 | 5/2007 | Devengenzo et al. | |
| 2007/0156123 A1* | 7/2007 | Moll | A61B 17/0057 606/1 |
| 2007/0197896 A1* | 8/2007 | Moll | A61B 1/00039 600/407 |
| 2010/0175701 A1 | 7/2010 | Reis et al. | |
| 2011/0290855 A1 | 12/2011 | Moore et al. | |
| 2013/0211397 A1* | 8/2013 | Parihar | A61B 18/18 606/33 |

FOREIGN PATENT DOCUMENTS

| | | |
|---|---|---|
| WO | WO-2004008611 A1 | 1/2004 |
| WO | WO-2010081050 A1 | 7/2010 |

OTHER PUBLICATIONS

International Search Report and Written Opinion for Application No. PCT/US2013/043617, mailed on Sep. 5, 2013, 15 pages.

(Continued)

*Primary Examiner* — Terence Boes

(57) ABSTRACT

A robotic assembly is configured to support, insert, retract, and actuate a surgical instrument mounted to the robotic assembly. The robotic assembly includes an instrument holder base member, a motor housing moveably mounted to the instrument holder base member, a carriage drive mechanism operable to translate the motor housing along the instrument holder base member, a plurality of drive motors, and a plurality of output drive couplings driven by the drive motors. One or more of the drive motors includes one or more magnetic flux shields to inhibit magnetic interference with an adjacent drive motor and/or with an adjacent motor orientation sensor.

10 Claims, 21 Drawing Sheets

(56) References Cited

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Partial European Search Report for Application No. 13797353.3, mailed on Dec. 21, 2015, 6 pages.

* cited by examiner

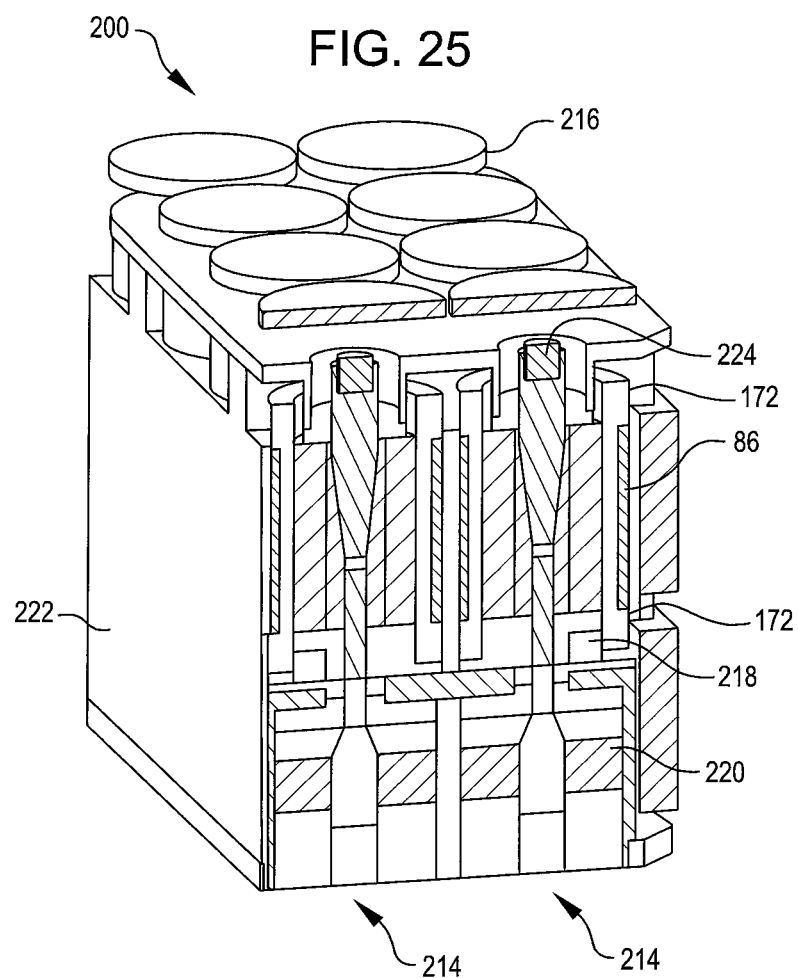

INSTRUMENT CARRIAGE ASSEMBLY FOR SURGICAL SYSTEM

CROSS-REFERENCES TO RELATED APPLICATIONS

This application claims the benefit of U.S. provisional application No. 61/654,391, filed Jun. 1, 2012, the entirety of which is incorporated by reference herein.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system available from Intuitive Surgical, Inc. of Sunnyvale, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601; the full disclosures of which are incorporated herein by reference.

A variety of structural arrangements can also be used to support and position the robotic surgical manipulator and the surgical instrument at the surgical site during robotic surgery. Supporting linkage mechanisms, sometimes referred to as set-up joints, or set-up joint arms, are often used to position and align each manipulator with the respective incision point in a patient's body. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, the full disclosures of which are incorporated herein by reference.

While the new telesurgical systems and devices have proven highly effective and advantageous, still further improvements are desirable. In general, improved minimally invasive robotic surgery systems are desirable. It would be particularly beneficial if these improved technologies enhanced the efficiency and ease of use of robotic surgical systems. For example, it would be particularly beneficial to increase maneuverability, improve space utilization in an operating room, provide a faster and easier set-up, inhibit collisions between robotic devices during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Robotic assemblies are disclosed that support, insert, retract, and actuate a surgical instrument mounted to the robotic assembly. The robotic assemblies include drive motors that are mounted in a common motor housing in a compact pattern. In many embodiments, the drive motors include magnetic flux shields that inhibit interference between adjacent drive motors. As a result, the drive motors can be independently driven to articulate a corresponding portion of the surgical instrument without causing unintended articulation of other portions of the surgical instrument. And in many embodiments, sensor assemblies are included that directly monitor the orientation of output couplers used to actuate the surgical instrument. As a result, the absolute orientation of the output couplers can be readily determined—a capability that is useful when resetting a surgical system such as may be required in certain circumstances, for example, after a power failure. Additionally, in many embodiments, the disclosed robotic assemblies provide high actuation power and unlimited actuation range of motion from compact assemblies, thereby enabling use with advanced surgical instruments such as surgical staplers and vessel sealers.

Thus, in one aspect, a robotic assembly is disclosed that is configured to support, insert, retract, and actuate a surgical instrument mounted to the robotic assembly. The robotic assembly includes an instrument holder base member, a motor housing, a carriage drive mechanism, a plurality of drive motors, and a plurality of output drive couplings. The motor housing is moveably mounted to the instrument holder base member. The carriage drive mechanism is operable to selectively translate the motor housing relative to the instrument holder base member along an insertion axis of the surgical instrument. Each of the drive motors is mounted to the motor housing. One or more of the drive motors includes a magnetic flux shield. Each of the output drive couplings is drivingly coupled with a corresponding one of the drive motors. Each of the output drive couplings is configured to drivingly couple with a corresponding input drive coupling of the surgical instrument.

In many embodiments, the drive motors are configured to have high power density. For example, in many embodiments, at least one of the drive motors includes a brushless component motor having a trapezoidal-commutation motor constant (Km) greater than or equal to 1.25 oz.-in/Watts^½, where Km=(Trapezoidal Commutation Torque Constant in oz.-in/Ampere/(square root of phase-to-phase winding resistance in Ohms).

In many embodiments, one or more magnetic flux shields are configured and placed to effectively contain magnetic flux to inhibit magnetic interference between motors and/or between motors and sensor assemblies. In many embodiments, a ferrous ring is used as a flux shield. In many embodiments, one or more of the drive motors includes two magnetic flux shields that are disposed at opposite ends of the drive motor. Each of the flux shields can include a ring made of a magnetically soft material containing at least one of iron, cobalt, or nickel. In some embodiments, the flux shield can be a monolithic ferrous component providing the flux shielding function of more than one motor. In some embodiments, two such monolithic flux shields are provided, one providing the shield function for one end of two or more motors (e.g., two, three, four, five, etc.) while the second shield component provides the shield function for the opposite end of the same two or more motors.

In many embodiments, the drive motors are positioned in close proximity to one or more adjacent drive motors. For example, in many embodiments, two or more of the drive motors are separated by less than five millimeters. And in many embodiments, two or more of the drive motors are separated by less than two millimeters.

In many embodiments, there are at least five drive motors and each of the five drive motors is separated from at least two of the other drive motors by less than five millimeters. And in many embodiments, each of the five drive motors is separated from at least two of the other drive motors by less than two millimeters.

In another aspect, a robotic assembly is disclosed that is configured to support, insert, retract, and actuate a surgical instrument mounted to the robotic assembly. The robotic assembly includes an instrument holder base member, a motor housing, a carriage drive mechanism, a plurality of drive motors, a plurality of gear boxes, a plurality of output drive couplings, and a sensor assembly. The motor housing is moveably mounted to the instrument holder base member. The carriage drive mechanism is operable to selectively translate the motor housing relative to the instrument holder base member along an insertion axis of the surgical instrument. Each of the drive motors is mounted to the motor housing. Each of the gear boxes is drivingly coupled with a one of the drive motors. Each of the output drive couplings is drivingly coupled with a corresponding one of the gear boxes. Each of the output drive couplings is configured to drivingly couple with a corresponding input drive coupling of the surgical instrument. The sensor assembly includes an orientation sensor, a sensor target, and a sensor shaft. The sensor shaft drivingly couples the sensor target to a corresponding one of the output drive couplings through an aperture in an outer housing of the corresponding gear box. The sensor shaft is driven by an output link of the corresponding gear box that rotates in unison with the corresponding output drive coupling. In many embodiments, the orientation sensor optically reads the sensor target and reports the absolute rotational position to a control system.

In many embodiments, the robotic assembly includes a plurality of sensor assemblies. Each of the sensor assemblies includes an orientation sensor, a sensor target, and a sensor shaft. Each sensor shaft drivingly couples the corresponding sensor target to a corresponding one of the output drive couplings through an aperture in an outer housing of the corresponding gear box. Each sensor shaft is driven by an output link of the corresponding gear box that rotates in unison with the corresponding output drive coupling. In a preferred embodiment, the orientation sensor shaft is coupled to the output drive coupling with a gear ratio of exactly 1:1.

In many embodiments, the gear boxes are compact and/or efficient. For example, the gear ratio between at least one of the motors and the corresponding output drive coupling can be less than 40 to 1. And each of the output gear boxes can have two or fewer gear reduction stages.

In many embodiments, the drive motors are disposed between the orientation sensors and the output drive couplings. In such embodiments, each of the sensor shafts can be drivingly coupled to the corresponding output drive coupling via a sensor shaft gear that extends through the aperture in the corresponding outer housing to engage an output gear that rotates in unison with the corresponding output drive coupling. In many embodiments, two of the sensor shaft gears overlap along a shaft direction parallel to rotation axes of the sensor shafts. One or more of the corresponding apertures and output gears can be configured to accommodate the overlap of the sensor shaft gears along the shaft direction.

In many embodiments, the gear boxes include a planetary gear box. The planetary gear box can include a shaft bearing configured to react moment so as to inhibit an axis of rotation of an inner race of the shaft bearing from becoming misaligned with an axis of rotation of an outer race of the shaft bearing. In many embodiments, the shaft bearing includes two rows of rolling elements. In many embodiments, the planetary gear box includes a carrier gear that has external teeth that are engaged by a sensor shaft gear extending through the aperture. The sensor shaft gear is drivingly coupled with the sensor shaft.

In another aspect, a robotic assembly is disclosed that is configured to support, insert, retract, and actuate a surgical instrument mounted to the robotic assembly. The robotic assembly includes an instrument holder base member, a motor housing, a carriage drive mechanism, five drive motors, five gear boxes, five output drive couplings, and five sensor assemblies. The motor housing is moveably mounted to the instrument holder base member. The carriage drive mechanism is operable to selectively translate the motor housing relative to the instrument holder base member along an insertion axis of the surgical instrument. Each of the drive motors is mounted to the motor housing. Each of the gear boxes is drivingly coupled with a one of the drive motors. Each of the output drive couplings is drivingly coupled with a corresponding one of the gear boxes. Each of the output drive couplings is configured to drivingly couple with a corresponding input drive coupling of the surgical instrument. In some embodiments, this driving function is provided through an intermediate mechanical sterile adapter coupling device, which provides separation of the non-sterile drive coupling from the sterile surgical instrument. Each sensor assembly includes an orientation sensor and a sensor shaft. Each sensor shaft drivingly couples the orientation sensor to a corresponding one of the output drive couplings through an aperture in an outer housing of the corresponding gear box. Each sensor shaft is driven by an output link of the corresponding gear box that rotates in unison with the corresponding output drive coupling.

In many embodiments, one or more of the axes of the output drive couplings are parallel. For example, one or more of the axes of the output drive couplings can be substantially parallel with the insertion axis.

In many embodiments, the output drive couplings are arranged in a particular manner. For example, in many embodiments, the output drive couplings are arranged in a pattern with four corner output drive couplings and a central output drive coupling disposed between the four corner output drive couplings. In many embodiments, a maximum of two output drive couplings are stacked in a width direction of the motor housing.

In many embodiments, the robotic assembly includes a radio frequency identification (RFID) antenna module. The RFID antenna module can be configured to read an instrument RFID tag at any suitable range, for example, at a close range such as between 0 mm and approximately 20 mm separation distance.

In many embodiments, the robotic assembly includes a circuit board that includes the five orientation sensors of the five sensor assemblies. In many embodiments, the circuit board further includes five rotor orientation sensors where each of the rotor orientation sensors is configured to monitor the absolute angular orientation of a rotor of a corresponding one of the five drive motors.

The robotic assembly can be configured to drive a two-finger surgical instrument. For example, each of two of the output drive couplings that are furthest away from the insertion axis can be used to actuate a corresponding finger of a two-finger surgical instrument. The relative motions of the two fingers combine to provide both grip and yaw motions of a surgical end effector of the two-finger surgical instrument.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 8 shows the as installed arrangement of drive motors of the carriage assembly of FIG. 6.

FIG. 9 shows planetary gear boxes attached to the drive motors of FIG. 8.

FIG. 10 shows sensor shafts coupled to output gears of the planetary gear boxes of FIG. 9.

FIG. 11 shows a motor housing supporting the components of FIG. 10.

FIG. 12 is an exploded view illustrating a resolver assembly that monitors the rotational orientation of the drive motors of the carriage assembly of FIG. 6.

FIG. 13 shows the installed resolver assembly of FIG. 12.

FIG. 14 is an exploded view illustrating an orientation sensor assembly that monitors the rotational orientation of the sensor shafts of FIG. 10.

FIG. 15 shows the installed orientation sensor assembly of FIG. 14.

FIG. 16 shows an electronic control assembly, a radio frequency identification (RFID) antenna, and a contact assembly for the carriage assembly of FIG. 6.

FIG. 17 and FIG. 18 show outer housing components of the carriage assembly of FIG. 6.

FIG. 25 shows a drive assembly of the carriage assembly of FIG. 24.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
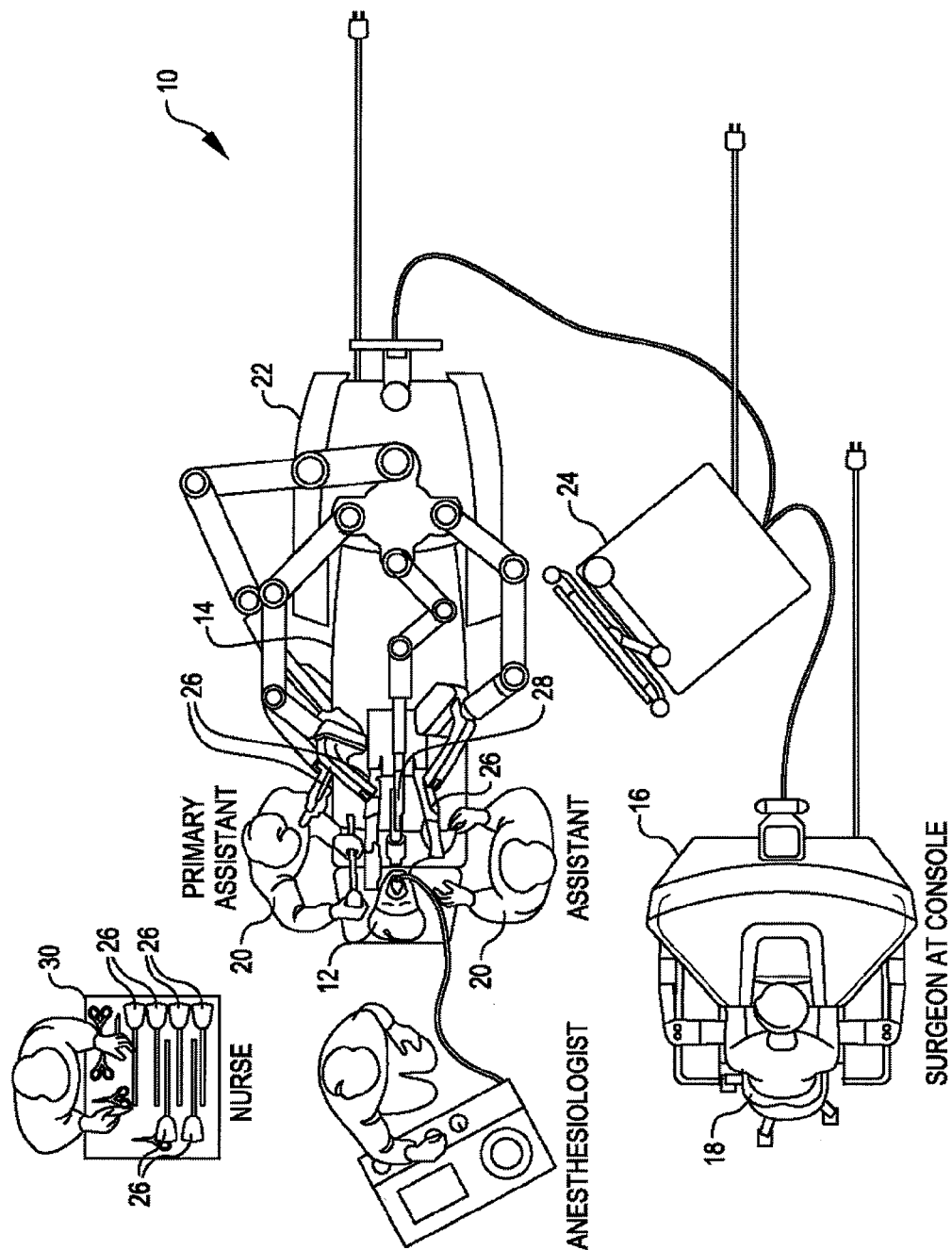
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
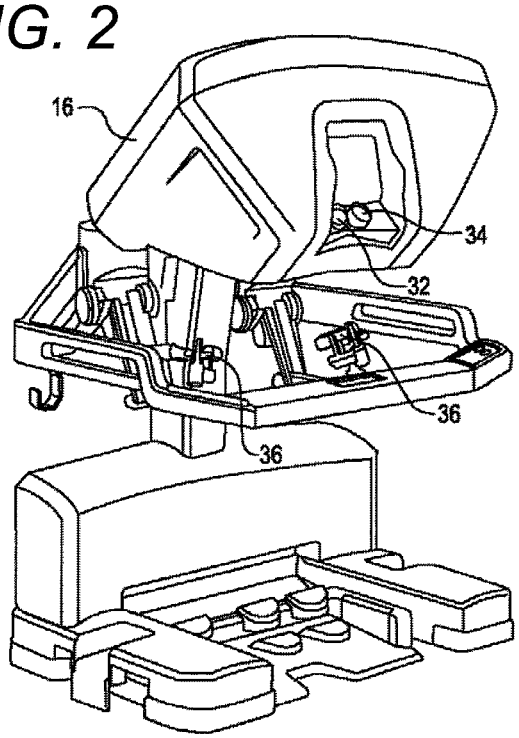
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
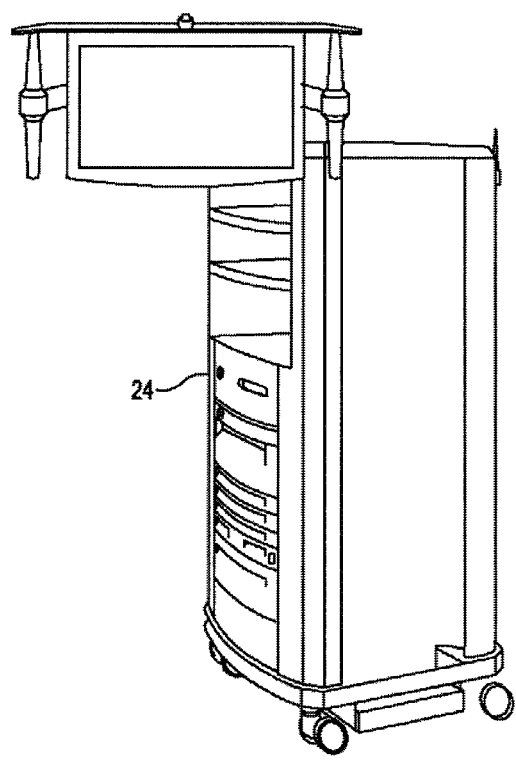
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
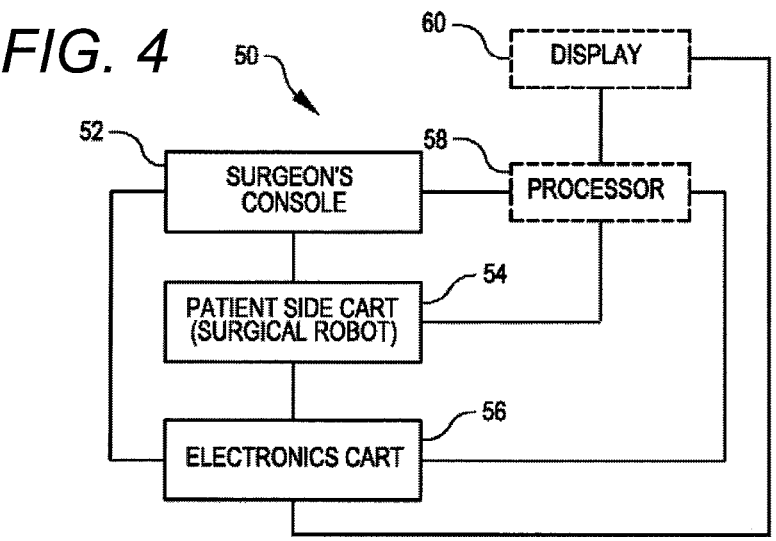
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
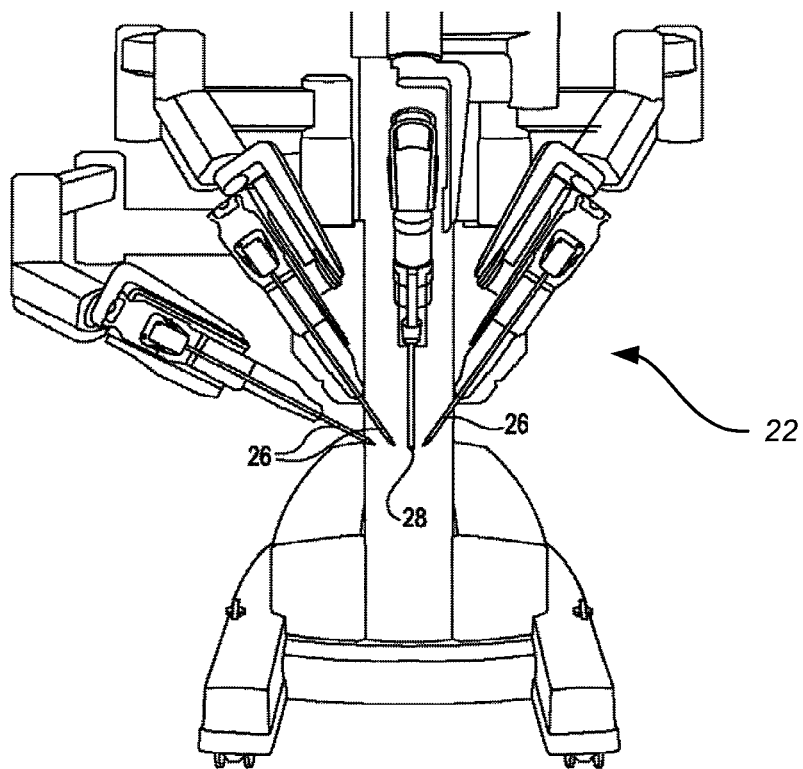
FIG. 5A is a partial view of a patient side cart (surgical robot) of a robotic surgery system, in accordance with many embodiments.
Figure 5B:
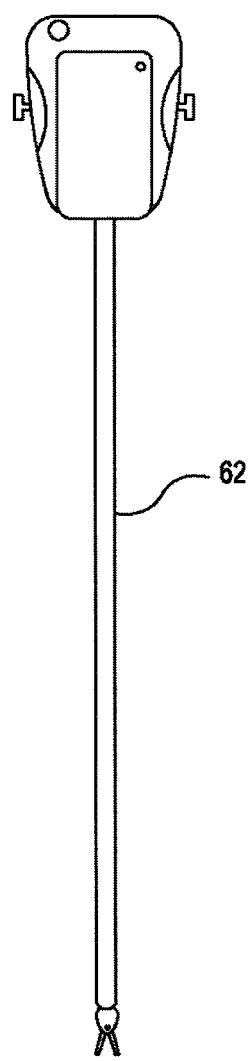
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Instrument Carriage Assemblies

Figure 6:
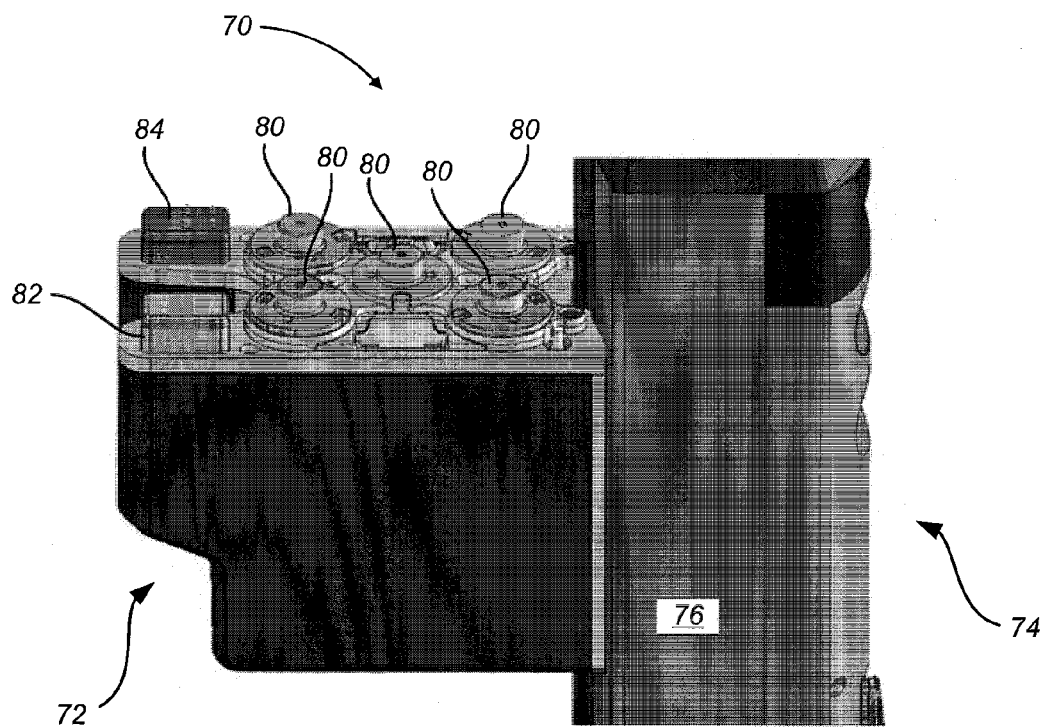
FIG. 6 shows a robotic assembly, in accordance with many embodiments, that includes a carriage assembly slideably mounted to an instrument holder base member for selective translation along an insertion axis of a surgical instrument mounted to the carriage assembly.
Figure 7:
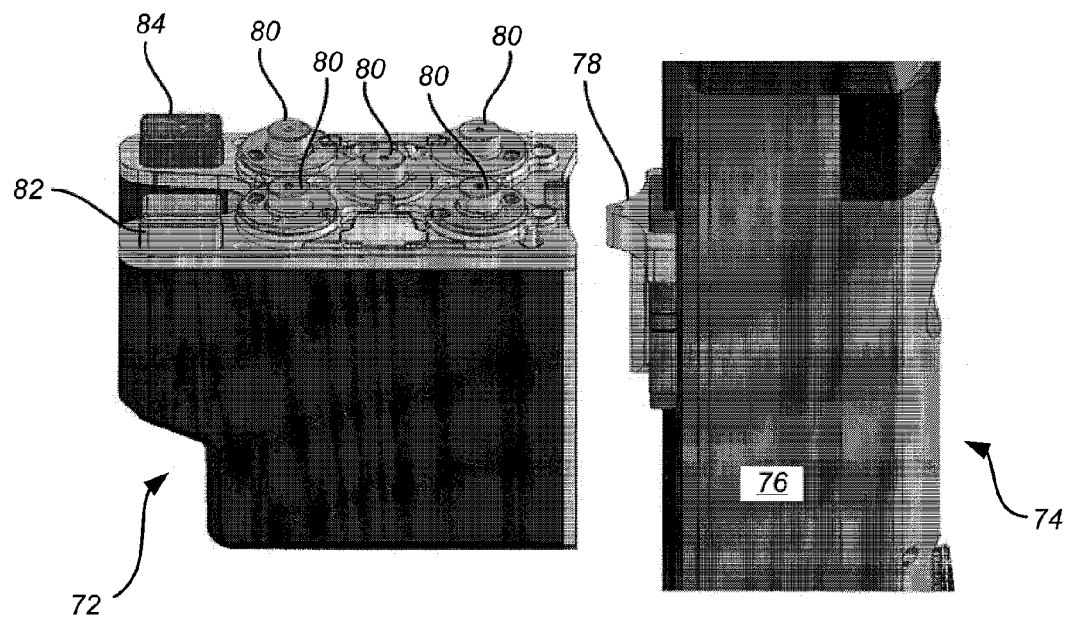
FIG. 7 shows the robotic assembly of FIG. 6 with the carriage assembly shown decoupled from the instrument holder base member.

FIG. 6 and FIG. 7 show a robotic assembly 70, in accordance with many embodiments, that includes a carriage assembly 72 and an instrument holder assembly 74. The instrument holder assembly 74 includes an instrument holder base member 76 and a spar fitting 78 slideably mounted to the instrument holder base member 76. The carriage assembly 72 is mountable to the spar fitting 78. The instrument holder assembly 74 includes a carriage drive mechanism (not shown) that is operable to selectively translate the spar fitting 78 along the instrument holder base member 76, thereby translating the carriage assembly 72 along the instrument holder base member 76 along an insertion axis of a surgical instrument (not shown) mounted to the carriage assembly 72.

The carriage assembly 72 includes five output drive couplings 80. Each of the output drive couplings 80 is configured to drivenly couple with a corresponding input drive coupling of a surgical instrument when the surgical instrument is mounted to the carriage assembly 72. Each of the five output drive couplings 80 can be independently actuated to actuate a corresponding mechanism of a mounted surgical instrument. For example, one of the output drive couplings 80 can be used to rotate an elongated shaft of the surgical instrument, one can be used to articulate an end effector of the mounted surgical instrument around a first axis (e.g., pitch axis), one can be used to articulate the end effector around a second axis (e.g., yaw axis) that is perpendicular to the first axis, one can be used to articulate a clamping jaw of the end effector, and one can be used to articulate a stapling and cutting cartridge of the end effector. In a preferred embodiment, the rotation axis of each of the five output drive couplings is substantially parallel to the elongate shaft of the surgical instrument. While the carriage assembly 72 includes five output drive couplings 80, a carriage assembly can be configured with any suitable number of output drive couplings.

In many embodiments, two of the output drive couplings can be configured to each drive a single finger of a two-finger surgical instrument. The relative motions of the two fingers combine to provide both grip and yaw motions of the surgical end effector. In many embodiments, the two output drive couplings furthest from the surgical instrument shaft are used to drive these grip/yaw motions.

Also in a preferred embodiment, the output drive couplings are arranged in an array so as to minimize the width of the carriage. For example, a maximum of two output drive couplings can be located adjacent to one another in a width direction of the carriage (see, for example, the arrangement of the drive couplings 80 in FIG. 6 where the two drive couplings at the right side of the array of five drive couplings 80 relative to the orientation of FIG. 6 are adjacent to one another in the width direction of the carriage and likewise the two drive couplings at the left side of the array five drive couplings 80 relative to the orientation of FIG. 6 are adjacent to one another in the width direction of the carriage).

The carriage assembly 72 also includes a radio frequency identification (RFID) antenna module 82 and a contact assembly 84. The RFID antenna module 82 can be used to interrogate an RFID tag on the surgical instrument or sterile adapter component, for example, to identify a mounted surgical instrument and/or to detect the presence of a mounted surgical instrument. The contact assembly 84 can connect to an identification chip of a mounted surgical instrument, for example, to identify a mounted surgical instrument and/or to detect the presence of a mounted surgical instrument or sterile adapter. In a preferred embodiment, the RFID antenna module 82 is designed to read the instrument RFID tag at close range, for example, between 0 mm and approximately 20 mm separation distance. The RFID tag signal can then be used as one (redundant) piece of information to help determine the approach, presence, and/or removal of the instrument from the carriage.

Figure 8:
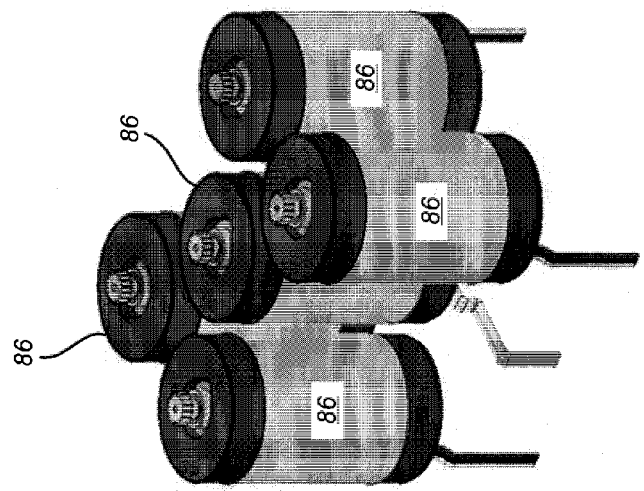

FIG. 8 shows the installed arrangement of drive motors 86 used to actuate the output drive couplings 80. In many embodiments, the drive motors 86 are electronically commutated motors (ECMs), which are controlled by associated electronic commutation systems. An ECM has permanent magnets that rotate and a fixed armature thereby eliminating the need to connect current to a moving armature. An electronic controller replaces the brush/commutator assembly of a brushed direct current (DC) motor. The orientation of the rotor for each of the drive motors 86 is monitored by a sensor assembly and supplied to an electronic controller for the drive motor. The drive motor orientation is used by the electronic controller to control the phase of the windings of the drive motor to control rotation of the drive motor. The drive motors 86 are arranged in a pattern with four corner drive motors and a central drive motor disposed between the four corner drive motors. In the illustrated arrangement, each of the four corner drive motors is disposed immediately adjacent to (e.g., separated by less than five millimeters, separated by less than two millimeters) an adjacent corner drive motor and the central drive motor. And the central drive motor is disposed immediately adjacent to each of the four corner drive motors. The arrangement provides open spaces on opposite sides of the central drive motor between two of the corner drive motors. In a preferred embodiment, the drive motors are a "component set" where the stator and rotor are individual components, forming a complete and functional motor only after being installed in the carriage housing.

Figure 9:
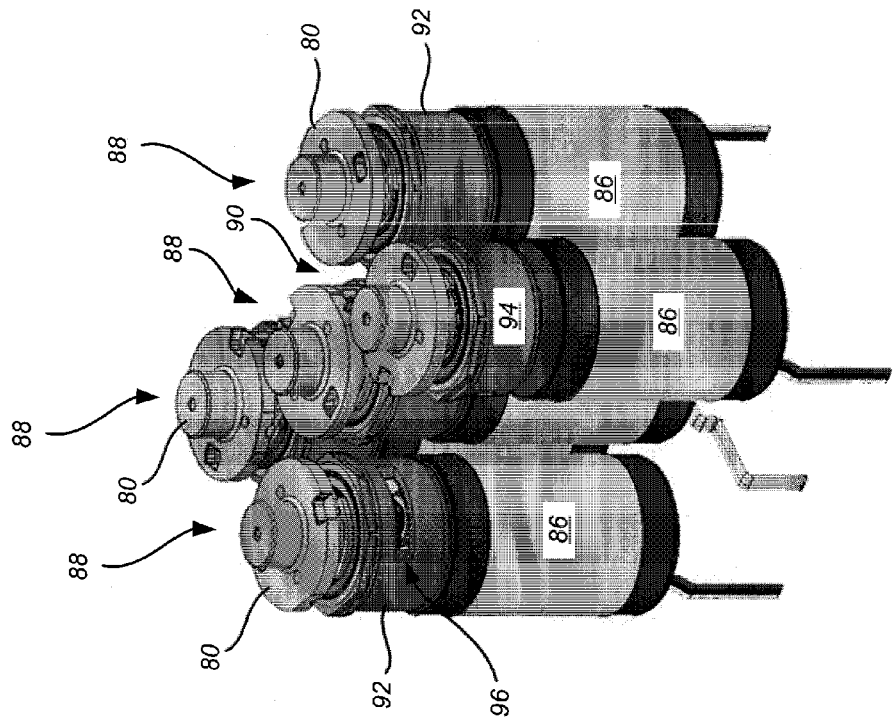
FIG. 8 through FIG. 18 is a sequence of figures that illustrate components of the carriage assembly of FIG. 6.

FIG. 9 shows output assemblies 88, 90 coupled to the drive motors 86. Each of four of the output assemblies (output assemblies 88) includes a spring-loaded output drive coupling 80 and a two-stage planetary gear box 92. The output assembly 90 includes a spring-loaded output drive coupling 80 and a single-stage planetary gear box 94. Each of the planetary gear boxes 92, 94 drivingly couple one of the spring-loaded output drive couplings 80 to a corresponding one of the drive motors 86. In many embodiments, the gear ratio of the output assembly gearbox is preferably less than 40:1 in order to provide high efficiency back-drivability. High efficiency back-drivability is an important feature enabling high performance surgical motions. In a preferred embodiment, each of the two-stage planetary gear boxes 92 provides an approximately 28 to 1 gear reduction. The single-stage planetary gear box 94 provides an approximately 5.3 to 1 gear reduction. Each of the planetary gear boxes 92, 94 includes an outer housing that has a slotted aperture 96 (most of which are hidden relative to the view direction of FIG. 9) that is aligned with a carrier gear having external gear teeth configured to drive pinion gears that extend through the slotted aperture 96. Each of the externally-geared carrier gears are output links for the planetary-gear boxes 92, 94 and therefore rotate in unison with the corresponding output drive coupling 80.

Figure 10:
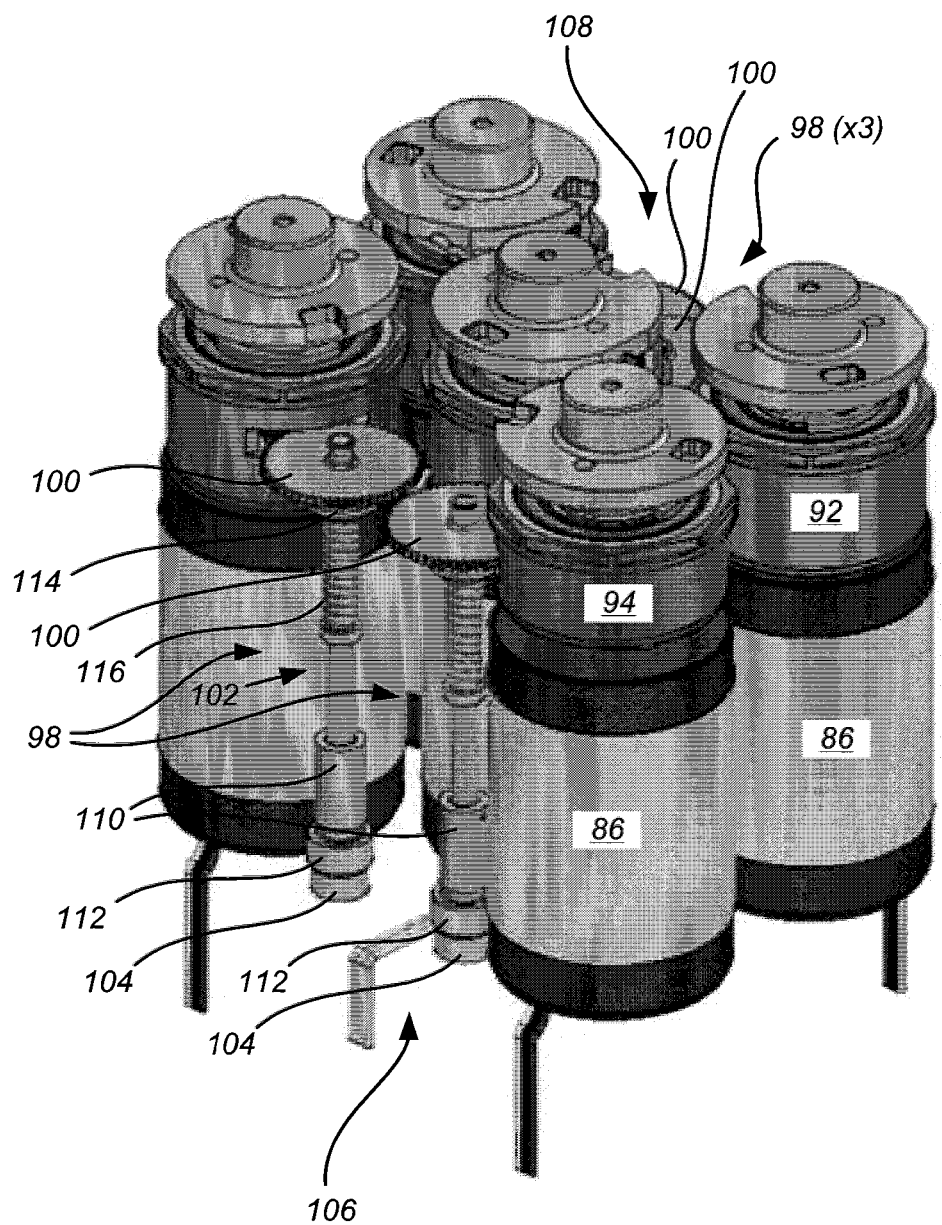

FIG. 10 shows five sensor assemblies 98 drivingly coupled to the externally-geared carrier gears of the planetary-gear boxes 92, 94. Each of the sensor assemblies 98 includes a pinion gear 100, a shaft assembly 102 coupled to the pinion gear 100, and a sensor target 104, the orientation of which is monitored by an absolute orientation sensor assembly (not shown). Each pinion gear 100 extends through one of the slotted apertures 96 to engage and be driven by the externally-geared carrier gear of the corresponding planetary gear box. The five drive motors 86 and associated planetary-gear boxes 92, 94 are arranged in a pattern that provides two open volumes 106, 108, which are located on opposite sides of the central drive motor. Each of the planetary gear boxes 92, 94 is oriented such that its slotted aperture 96 faces one of the open volumes 106, 108. Two of the sensor assemblies 98 are disposed in the near-side open volume 106. And three of the sensor assemblies 98 are disposed in the far-side open volume 108. The pinion gears 100 for the sensor assemblies 98 that engage the corner planetary gear boxes are located in the same geometric plane as shown for the two pinion gears 100 in the near-side open volume 106. The pinion gear 100 for the sensor assembly 98 that engages the central planetary gear box is disposed offset from and overlaps the other two pinion gears disposed in the far-side open volume 108. In many embodiments, the slotted apertures 96 have an increased width to accommodate the possible positions of the pinion gear 100 associated with the overlap between the pinion gears 100 disposed in the far-side open volume 108. Likewise, in many embodiments, the gear teeth of the externally-geared carrier gears have an increased width to accommodate the possible positions of the pinion gear 100 associated with the overlap between the pinion gears 100 disposed in the far-side open volume 108.

Each shaft assembly includes a drive shaft 110, a bottom end bearing 112, a top end bearing 114, and a compression spring 116. The top end bearing 114 can be translated along the drive shaft 110 thereby compressing the compression spring 116 to position the top end bearing 114 for lateral installation of the sensor assembly 98 into a motor housing (shown in FIG. 11). Once installed into the motor housing, extension of the compression spring 116 repositions the top end bearing 114 into engagement with a corresponding bearing receptacle in the motor housing.

Figure 11:
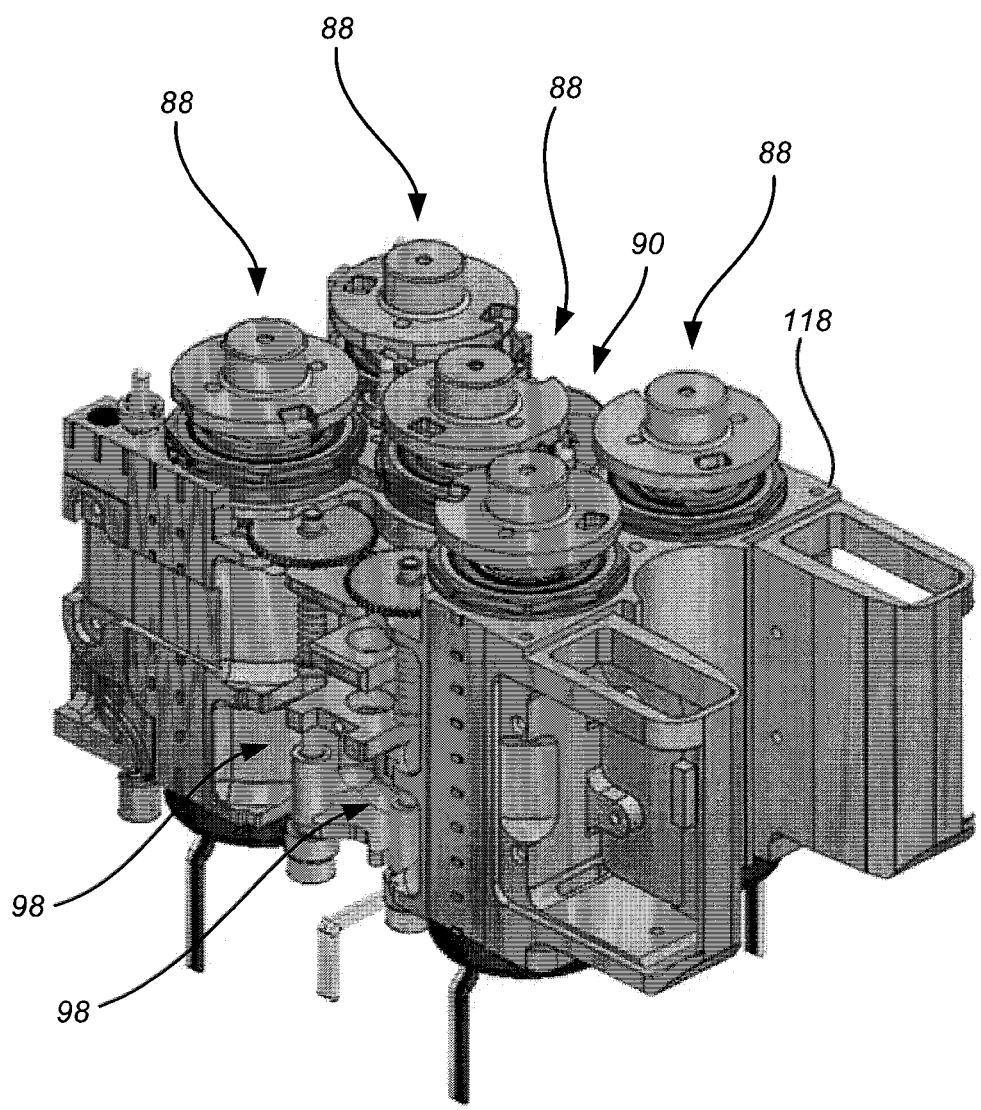

FIG. 11 shows the motor housing 118 with the drive motors 86, planetary gear boxes 92, 94, and the sensor assemblies 98 mounted to the motor housing 118. In many embodiments, the motor housing 118 is a monolithically machined component configured to accommodate and/or support the drive motors 86, the sensor assemblies 98, as well as other components of the carriage assembly 72. In a preferred embodiment, the monolithically machined motor housing 118 is made from a material having thermal conductivity greater than 70 W/m-K (e.g., magnesium or aluminum).

Figure 12:
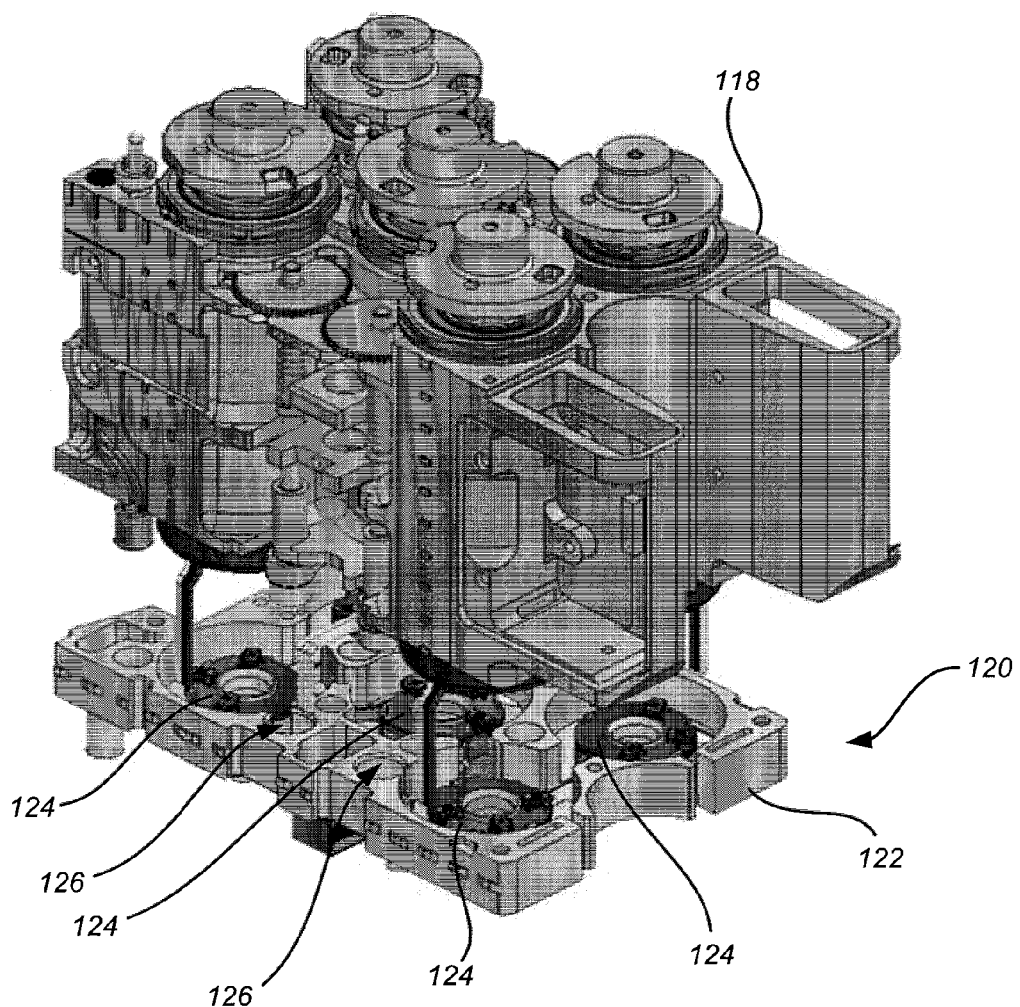
Figure 13:
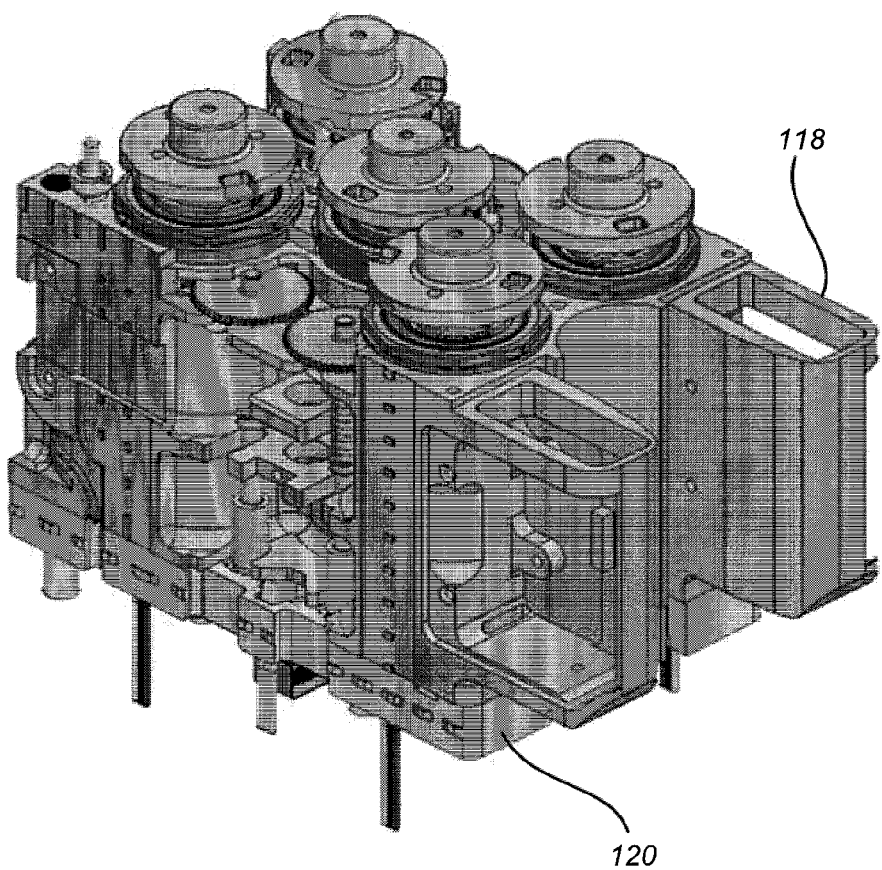

FIG. 12 is an exploded view showing a Hall-effect sensor assembly 120 that includes a mounting frame 122 and five Hall-effect sensors 124 mounted to the mounting frame 122. Each of the Hall-effect sensors 124 monitors the orientation of a rotor of the corresponding drive motor 86 by providing an output signal, which changes as the alternating North and South magnetic poles of the motor rotor pass by the sensor. An output signal from each of the Hall-effect sensors 124 is input to an electronic controller for the corresponding drive motor. Each of the electronic controllers uses the orientation signal to control the phase of the windings of the corresponding drive motor to control rotation of the drive motor. The mounting frame 122 also includes receptacles 126 that receive and support the bottom end bearings 112 of the five sensor assemblies 98. FIG. 13 shows the Hall-effect assembly 120 mounted to the motor housing 118.

Figure 14:
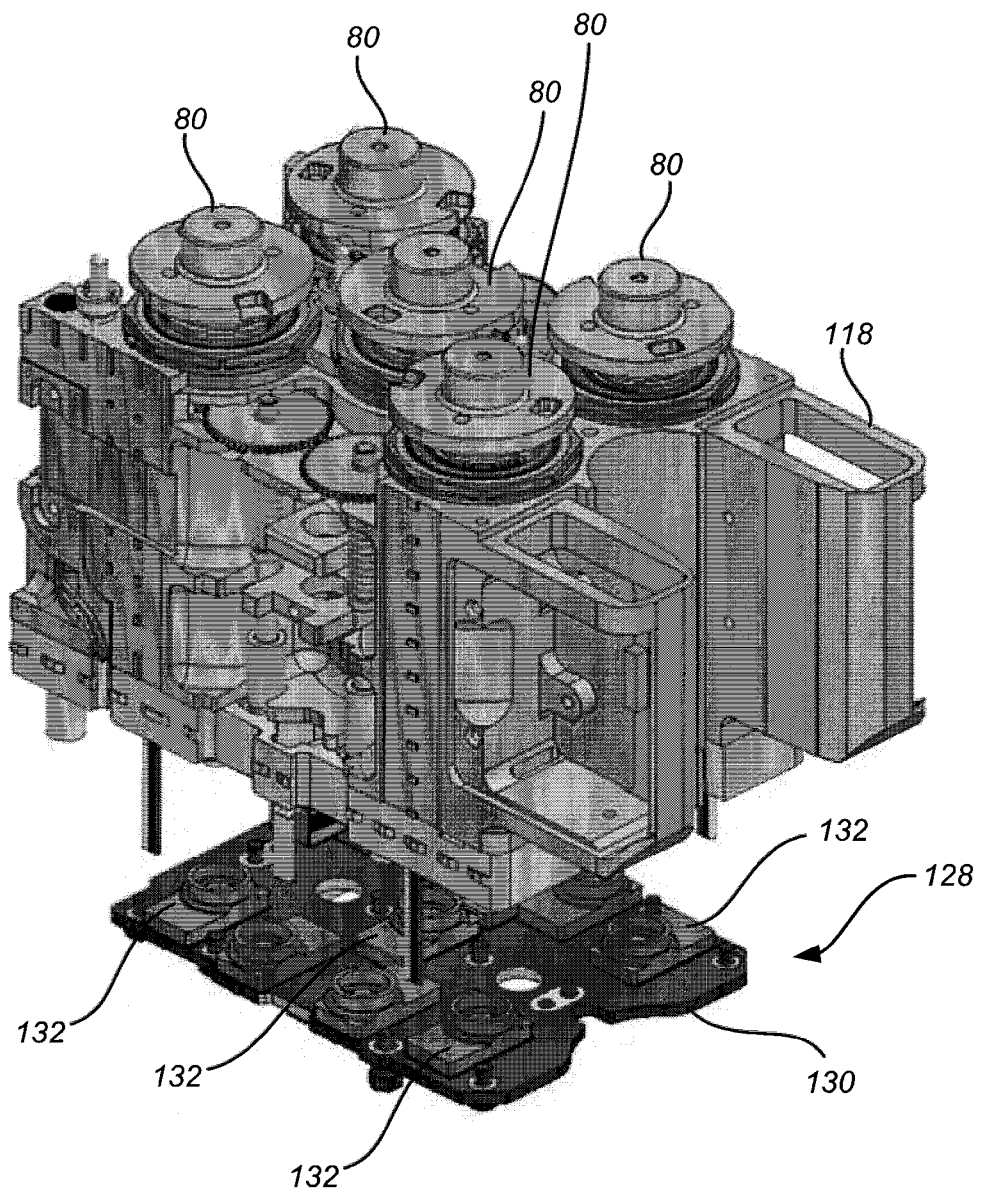
Figure 15:
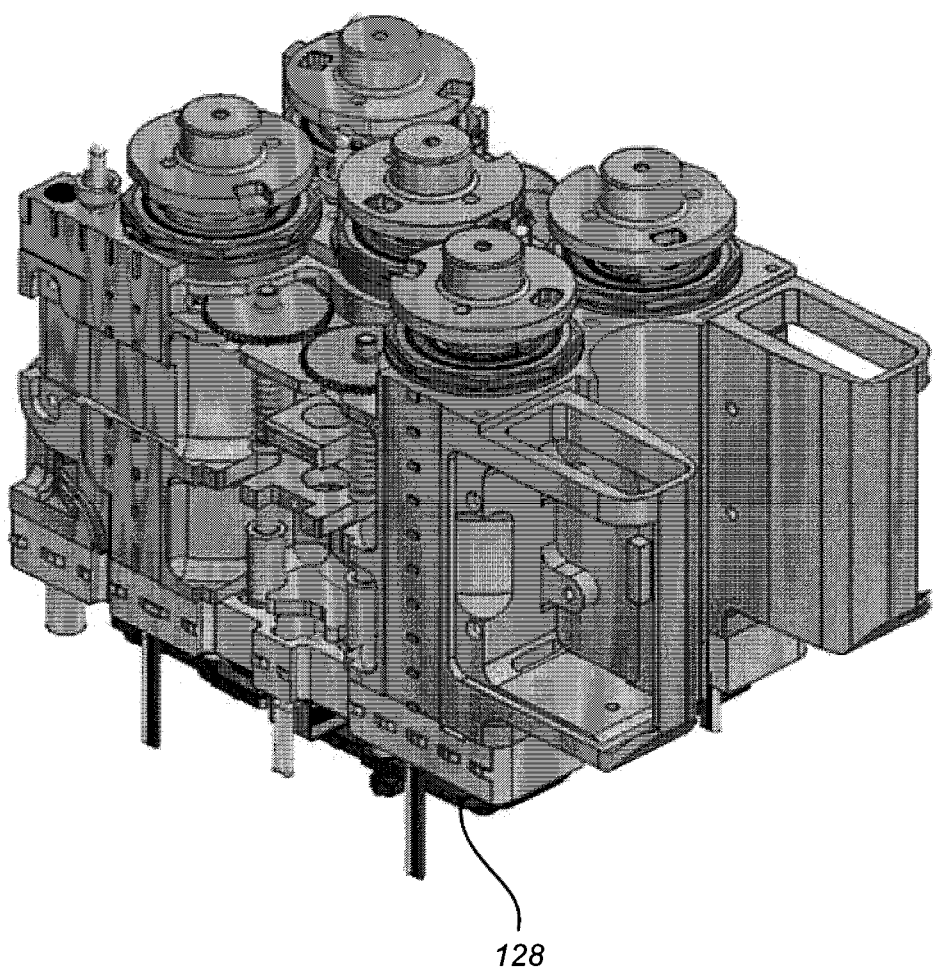

FIG. 14 is an exploded view showing an absolute orientation sensor assembly 128 that includes a mounting frame 130 and ten orientation sensors 132 mounted to the mounting frame. Five of the orientation sensors 132 monitors the orientation of a corresponding one of the sensor assemblies 98, thereby monitoring the orientation of the corresponding output drive coupling 80. Additionally, five of the orientation sensors monitor the orientation of the rotor component of the drive motor. These five orientation sensors provide a second means of motor rotation sensing in addition to the Hall-effect sensor assembly. In many embodiments, the orientation sensors 132 include optical sensors that sense the angular orientation of an optically readable pattern on the sensor target 104 of the corresponding sensor assembly 98, thereby sensing the orientation of the sensor target 104. FIG. 15 shows the orientation sensor assembly 128 mounted in its installed position.

Figure 16:
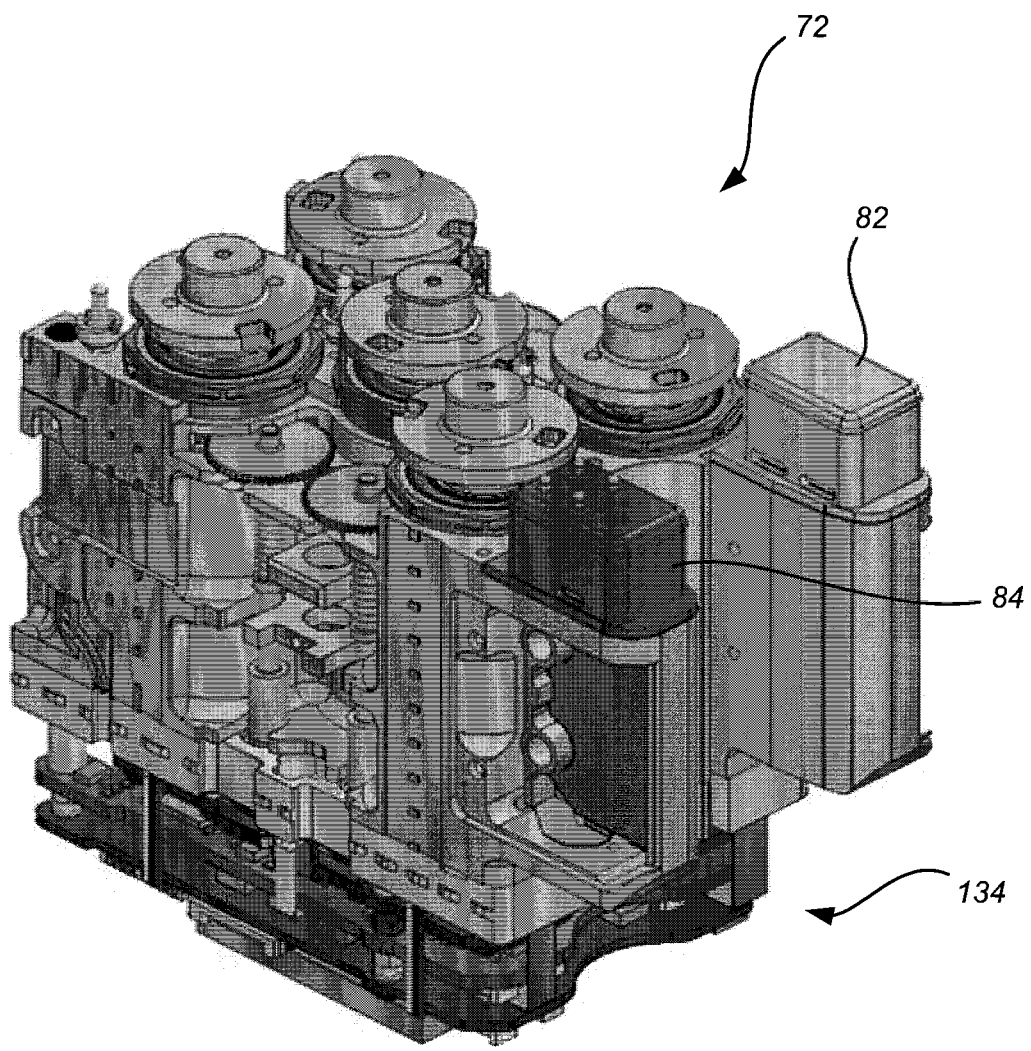
Figure 17:
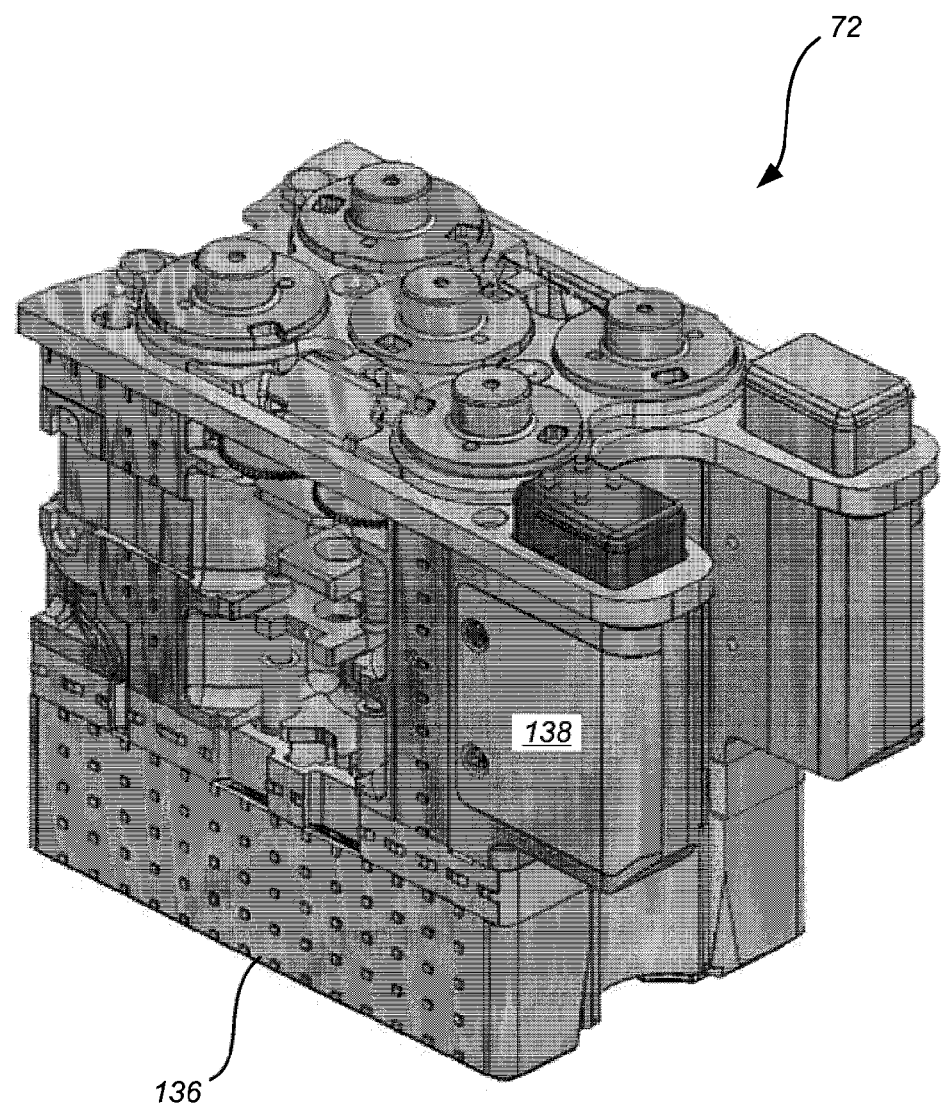
Figure 18:
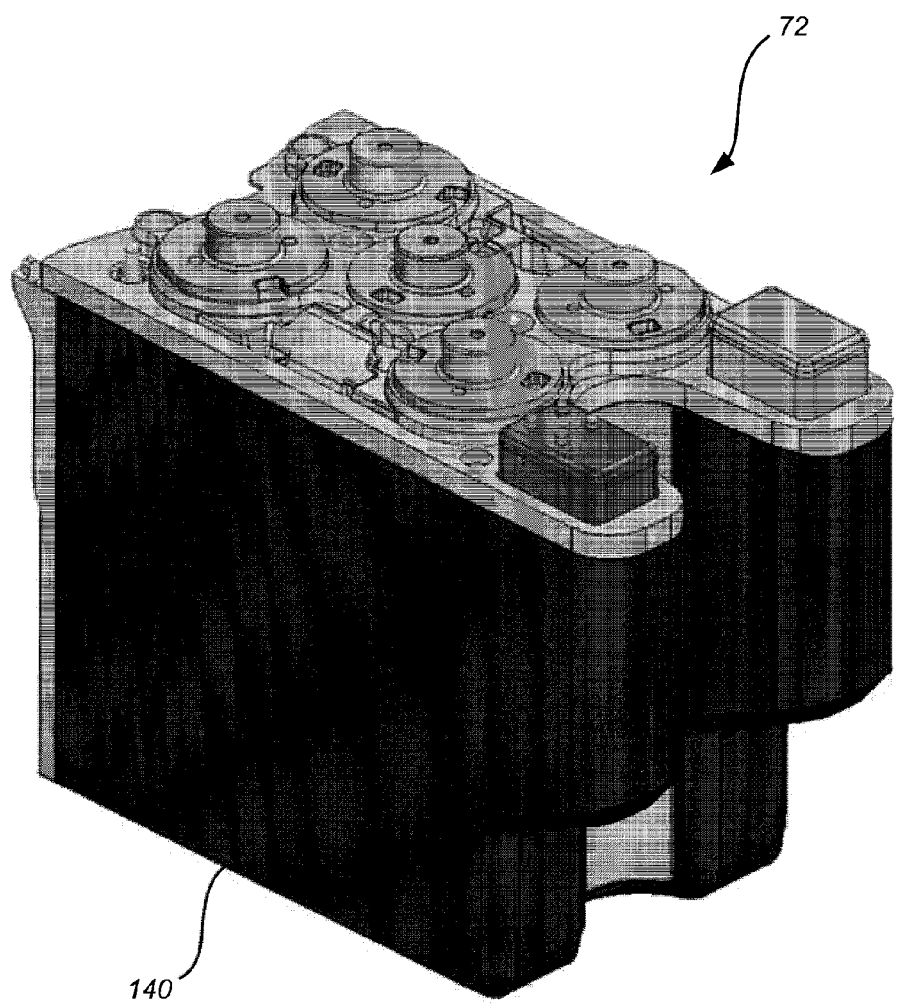

FIG. 16 through FIG. 18 show additional components of the carriage assembly 72. FIG. 16 shows the mounted positions of an electronic control assembly 134, the radio frequency identification (RFID) antenna module 82, and the contact assembly 84. FIG. 17 shows the mounted positions of a lower housing 136 and a side cover 138. And FIG. 18 shows the mounted positions of an outer housing 140.

Figure 19:
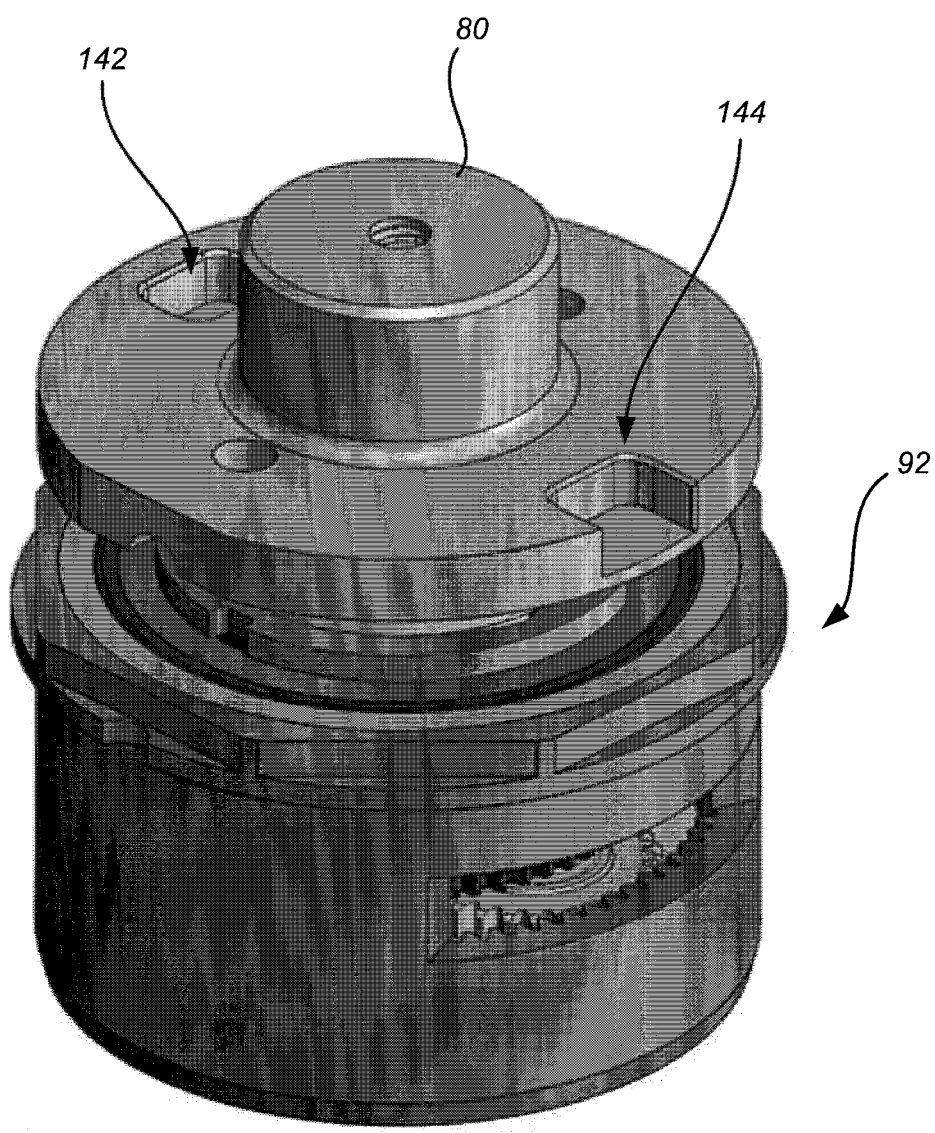
FIG. 19 shows one of the planetary gear boxes of FIG. 9.

FIG. 19 shows one of the two-stage planetary gear boxes 92 and an associated one of the output drive couplings 80. The output drive coupling 80 includes oppositely disposed drive receptacles 142, 144 that receive and drivingly coupled with corresponding drive extension features in a mating coupling. The drive receptacles 142, 144 are disposed at different radial positions, thereby ensuring only one possible angular orientation of engagement between the output drive coupling 80 and the corresponding mating coupling.

Figure 20:
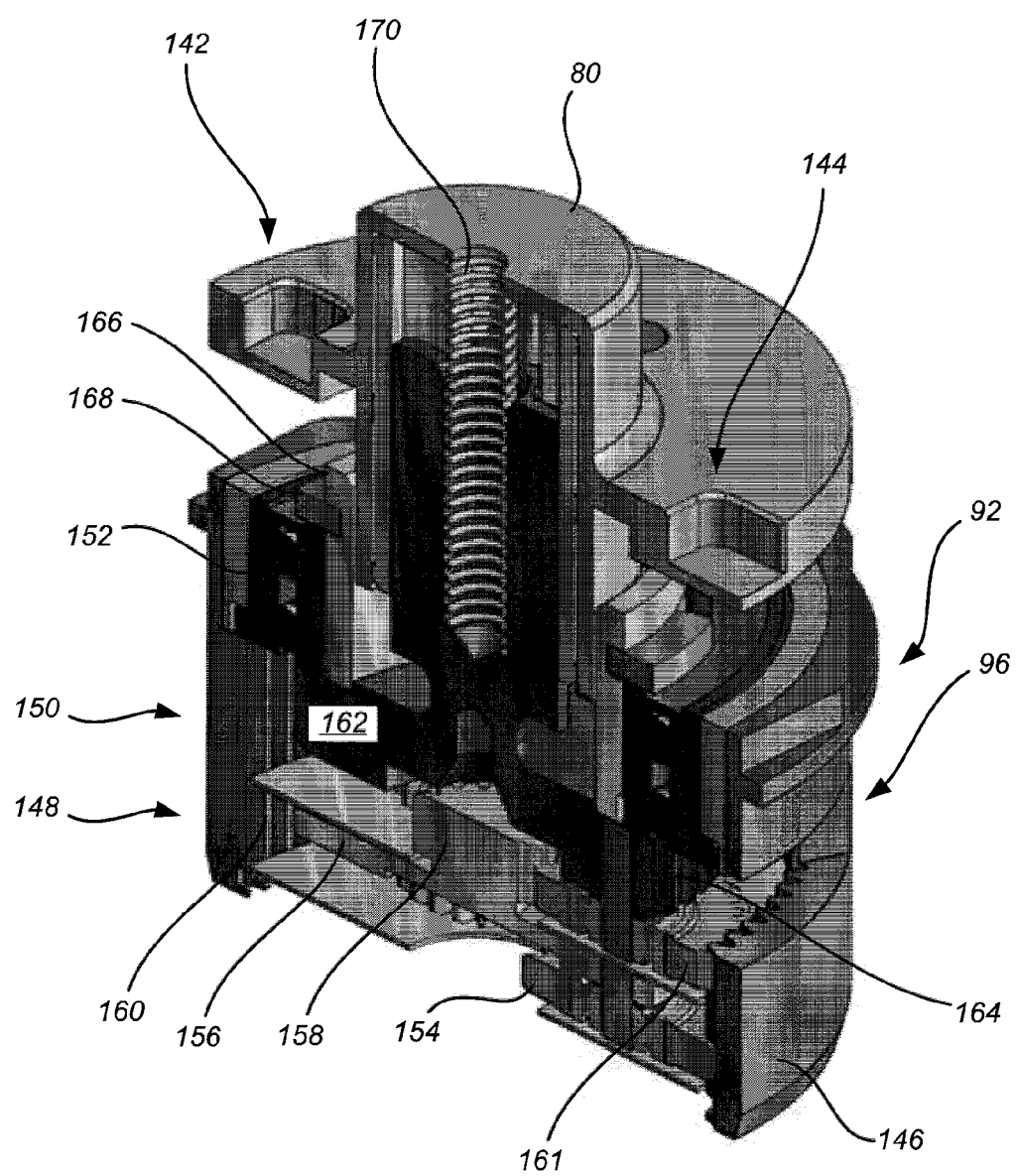
FIG. 20 shows a cross-section of the planetary gear box of FIG. 19.

FIG. 20 shows a cross-section of one of the two-stage planetary gear boxes 92. The planetary gear box 92 includes an outer housing 146, a first planetary stage 148, a second planetary stage 150, a double-row bearing 152. The first planetary stage 148 includes first stage planet gears 154 that interface with and are driven by a sun gear (not shown) mounted to the rotor of the corresponding drive motor 86. The first stage planet gears 154 are rotationally mounted to a first stage carrier 156 that is fixedly attached to a first stage output sun gear 158. The first stage planet gears 154 interface with an internal ring gear 160 integral to the outer housing 146. The second planetary stage 150 includes second stage planet gears 161 that interface with and are driven by the first stage output sun gear 158. The second stage planet gears 161 are rotationally mounted to a second stage carrier 162. The second stage planet gears 161 interface with the internal ring gear 160 integral to the outer housing 146. The second stage carrier 162 has external gear teeth 164 that interface with and drive the pinion gear 100 of the corresponding sensor assembly 98. The second stage carrier external gear teeth 164 and the aperture 96 in the outer housing 146 have a width in an axial direction of the planetary gear box 92 sized to accommodate different possible positions of the corresponding pinion gear 100 associated with the overlap of the pinion gears 100 as described herein.

The second stage carrier 162 is fixedly coupled to an inner hollow shaft 166 that interfaces with and is supported by an inner race of the double row bearing 152. A retainer ring 168 interfaces with a slot in the inner hollow shaft 166 and retains the assembly of the second stage carrier 162 and the inner hollow shaft 166 relative to the inner race of the double row bearing 152. The double row bearing 152 includes two rows of rolling elements, which serve to constrain the second stage carrier 162 to rotate concentric to the outer housing 146. With the additional rotational constraint provided by the double row bearing 152, the double row bearing 152 is used in place of two or more separate bearings, thereby allowing the planetary gear box 92 to have a smaller length along the axial direction of the planetary gear box 92 as compared to a traditional planetary gear box having two or more separate bearings.

The second stage carrier 162 is drivingly coupled with the output drive coupling 80 via external splines. A compression spring 170 biases the output drive coupling 80 into an extended position. The second stage carrier 162, the output drive coupling 80, and the compression spring 170 are configured so that the output drive coupling 80 can be displaced towards the planetary gear box 92 during an engagement process in which the output drive coupling 80 is rotated until oriented such that the drive receptacles 142, 144 are properly aligned with corresponding drive extension features in a mating coupling. The single-stage planetary gear box 94 is configured similar to the two-stage planetary gear box 92, but without the first planetary stage 148.

Figure 22:
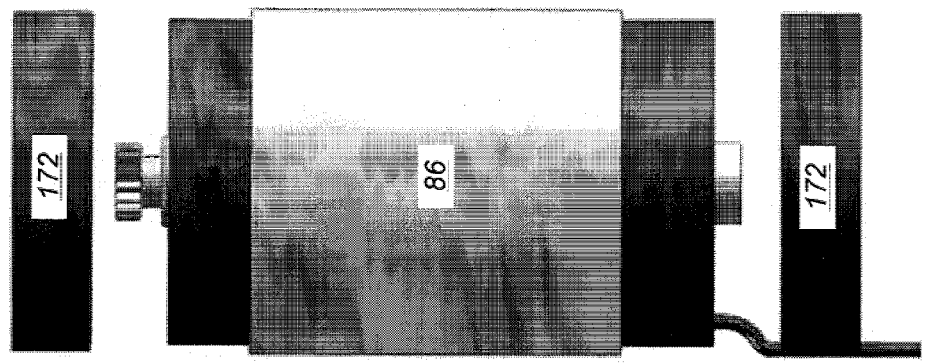
FIG. 22 is an exploded view of the drive motor of FIG. 21 and illustrates ferrous end rings that serve as magnetic flux shields.
Figure 21:
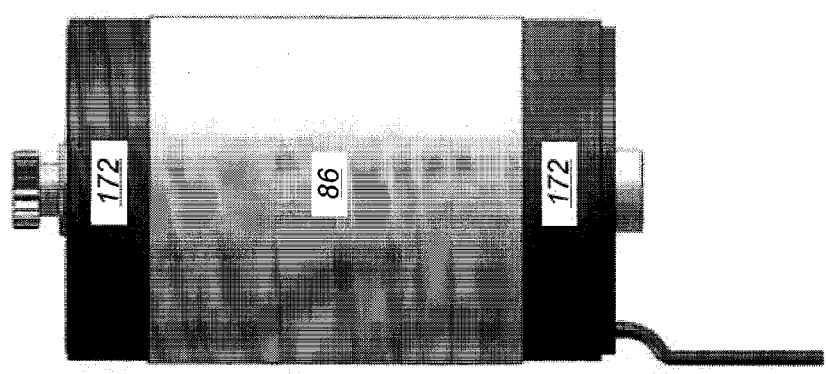
FIG. 21 shows one of the drive motors of FIG. 8.

FIG. 21 shows a side view of one of the drive motors 86. Each of the drive motors 86 includes magnetic flux shields 172 disposed at opposite ends of the drive motor. FIG. 22 is an exploded view showing the magnetic flux shields 172 displaced from the rest of the drive motor 86. In many embodiments, each of the magnetic flux shields 172 is made from a suitable magnetically soft material (e.g., iron, cobalt, and/or nickel) having suitably high magnetic permeability. In the illustrated embodiment, each magnetic flux shield 172 is configured as a thin hollow cylinder having the illustrated axial length relative to the axial length of the drive motor 86. The magnetic flux shields 172 are located at the ends of the drive motor 86 to entrain magnetic flux lines emanating from the magnetized motor rotor so that those magnetic flux lines do not extend adjacent to the drive motor 86 to interfere with an adjacent drive motor and/or interfere with an adjacent motor sensor.

Figure 23:
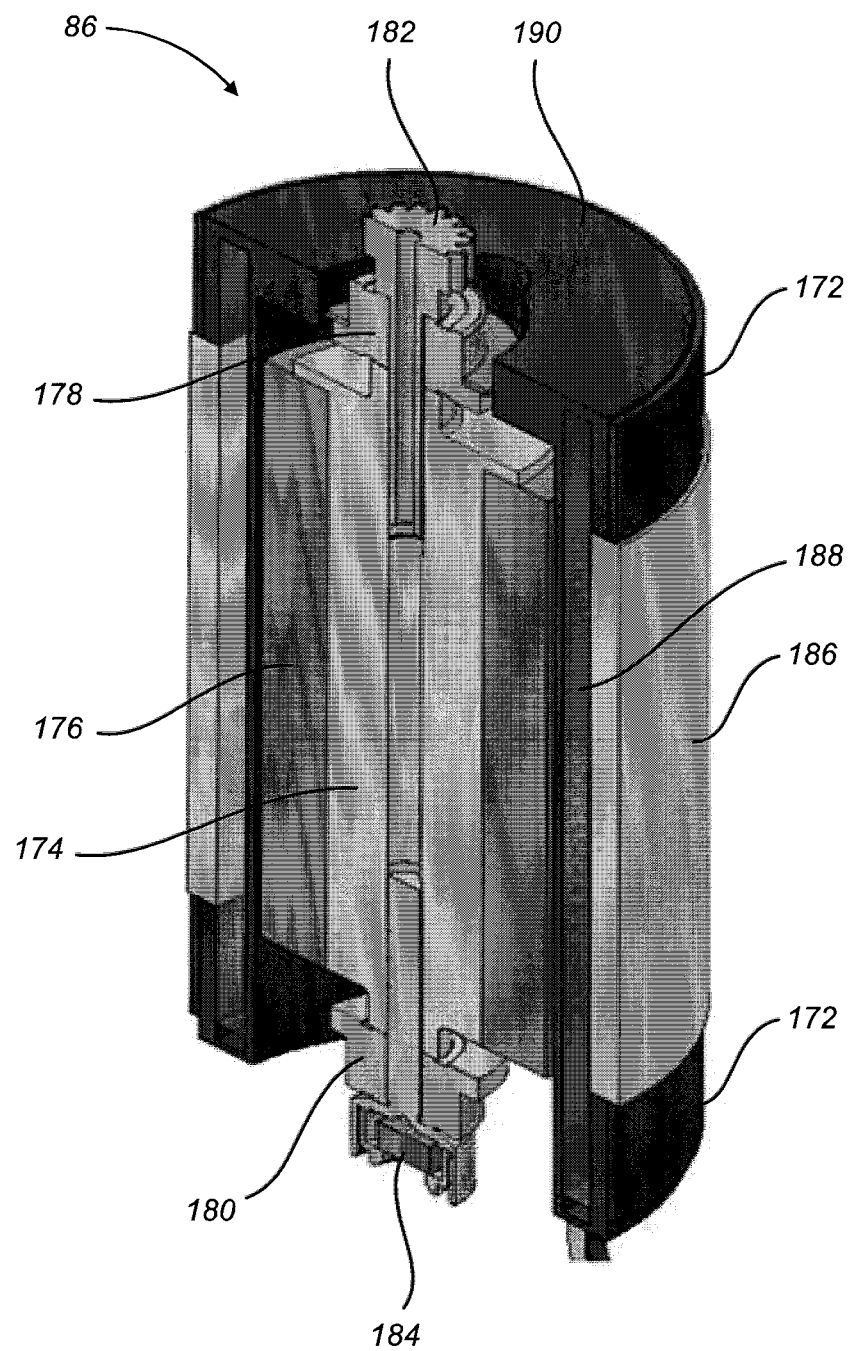
FIG. 23 shows a cross-section of the drive motor of FIG. 21.

FIG. 23 shows a cross section of one of the drive motors 86. The drive motor 86 includes a rotor 174 having permanent magnets 176, a top end bearing 178, a bottom end bearing 180, an output gear 182, an orientation sensor target 184 (note that this is the target for the optical encoders shown in FIG. 14 and NOT the Hall-effect sensors shown in FIG. 12), an outer motor housing 186 in which motor windings 188 are disposed, the magnetic flux shields 172, and an end cap 190. Each of the magnetic flux shields 172 is disposed at opposing ends of the drive motor 86 so as to overlap a corresponding end of the motor windings 188. The location and the configuration of the magnetic flux shields 172 is selected to inhibit and/or prevent magnetic flux lines emanating from the magnetized motor rotor from interacting with an adjacent drive motor(s) and/or with one or more adjacent motor orientation sensors. The shields prevent the magnetic fields coming from the permanent magnets on the rotor from interacting with adjacent motors and/or sensors. The magnetic field coming from the stator windings is generally far weaker than the rotating permanent magnet field of the rotor and is generally not the main source of detrimental interference. The shields, however, do serve to attenuate both effects.

Figure 24:
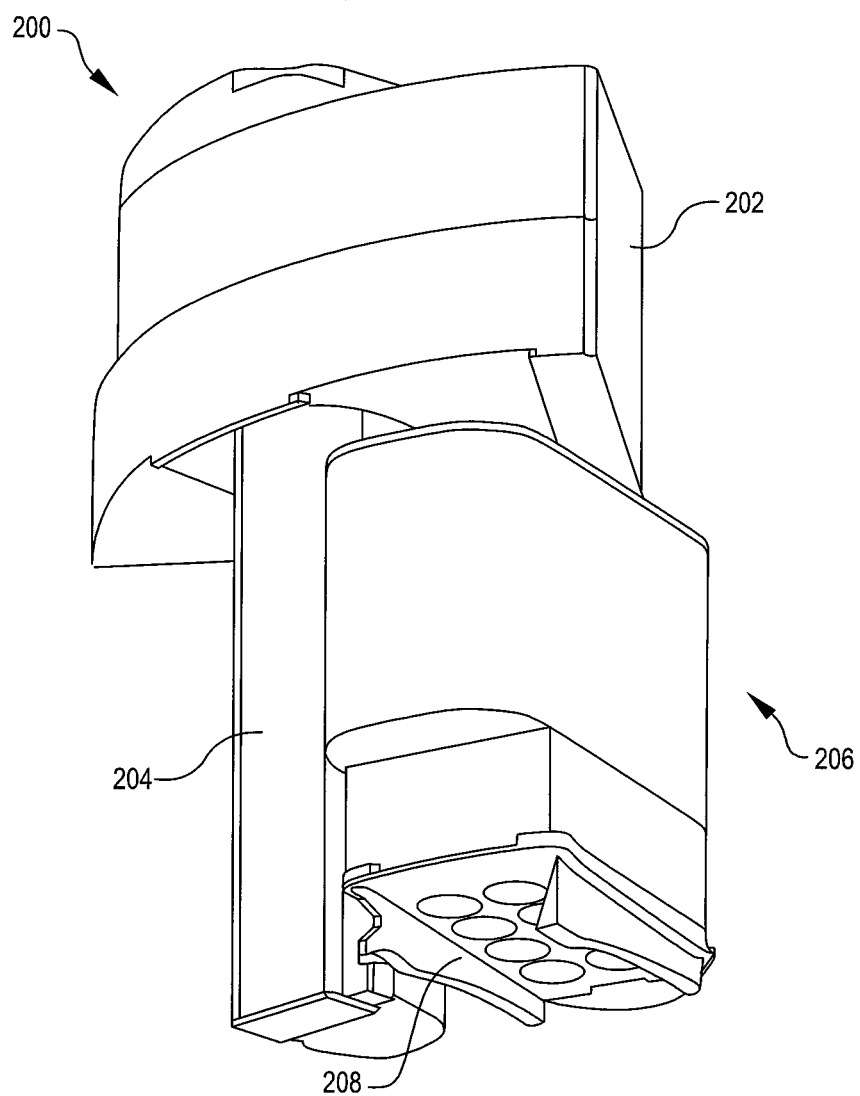
FIG. 24 shows a robotic assembly, in accordance with many embodiments, that includes a carriage assembly slideably mounted to an instrument holder base member for selective translation along an insertion axis of a surgical instrument mounted to the carriage assembly.

FIG. 24 shows a robotic assembly 200, in accordance with many embodiments. The robotic assembly 200 includes an insertion axis base 202, an insertion axis assembly 204, a carriage assembly 206, and a sterile adapter 208. The insertion axis assembly 204 is telescopic and attached to the insertion axis base 202, which can be selectively positioned and oriented via an upstream linkage (not shown). The carriage assembly 206 is mounted to the insertion axis assembly 204 and is selectively translatable along the insertion axis assembly 204. The carriage assembly 206 includes eight rotary drive assemblies configured to couple with and actuate up to a corresponding eight inputs of a surgical instrument (not shown) mounted to the carriage assembly 206. The sterile adapter 208 is configured to mount to the carriage assembly 206 by a snap-in interface design that provides for quick release of the sterile adapter 208. The sterile adapter 208 includes eight rotary couplers that drivingly couple outputs of the eight rotary drive assemblies of the carriage assembly to rotary drive inputs of a surgical instrument (not shown) mounted to the carriage assembly 206. In many embodiments, the eight rotary drive assemblies include six drive assemblies used to actuate up to six rotary drive inputs of a surgical instrument and two additional rotary drive assemblies that are used to drive additional rotary drive inputs of advanced surgical instruments (e.g., stapler, vessel sealer).

FIG. 25 shows a drive assembly 212 of the carriage assembly 206. The drive assembly 212 includes eight drive assemblies 214. Each of the drive assemblies 214 includes a drive motor 86, a primary angular orientation sensor 216, a secondary angular orientation sensor 218, and a planetary gear box 220. The eight drive motors 86 of the drive assembly 212 are arranged in a two wide by four deep array. The drive assembly 212 includes a motor housing 222 configured to accommodate and/or support the drive motors 86, the primary angular orientation sensors 216, the secondary angular orientation sensors 218, and the planetary gear boxes 220.

The drive motors 86 are configured similar to the drive motors 86 of the carriage assembly 72 discussed herein. As such, the description of the drive motors 86 of the carriage assembly 72 applies to the drive motors 86 of the drive assembly 212 and will therefore not be repeated here.

Any suitable angular orientation sensors can be used for the primary and secondary angular orientation sensors 216, 218. For example, in many embodiments, each of the primary angular orientation sensors 216 is an absolute magnetic encoder that includes a magnetic sensor that tracks the absolute orientation of a magnet 224 attached to a rotor of the corresponding drive motor 86. And in many embodiments, the secondary angular orientation sensors 218 are compact Hall Effects sensors. The angular orientation the drive motor 86 in each of the drive assemblies 214 is redundantly tracked by the primary and secondary angular orientation sensors 216, 218, thereby providing an increased confidence level to the tracking of the angular orientation of the drive motor 86.

The eight planetary gear boxes 220 are configured similar to the output assemblies 88, 90 of the carriage assembly 72 discussed herein. Notable differences include that the planetary gear boxes 220 include additional bearing assemblies distributed along the centerline of the gear box and are thus somewhat longer than the output assemblies 88, 90. The eight planetary gear boxes 220 are relatively heavy duty, highly back-drivable, efficient, have low backlash (e.g., 0.05 degree). Two planetary stages are used to produce a 28 to 1 gear reduction for standard low-speed drive assemblies 214 (e.g., seven of the eight drive assemblies 214). And one planetary stage is used to produce a 5.3 to 1 gear reduction for a low-speed drive assembly 214 (e.g., one of the eight drive assemblies).

As discussed herein, each of the drive motors 86 includes magnetic flux shields 172 disposed at the ends of the drive motors 86. The flux shields 172 serve to entrain magnetic flux lines emanating from the magnetized motor rotor so that those magnetic flux lines do not extend adjacent to the drive motor 86 to interfere with an adjacent drive motor and/or interfere with an adjacent primary and/or secondary angular orientation sensor 216, 218.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A robotic assembly configured to support, insert, retract, and actuate a surgical instrument mounted to the robotic assembly, the robotic assembly comprising:
   an instrument holder base member;
   a motor housing moveably mounted to the instrument holder base member;
   a carriage drive mechanism operable to selectively translate the motor housing relative to the instrument holder base member along an insertion axis of the surgical instrument;
   a plurality of drive motors, each of the drive motors being mounted to the motor housing; and
   a plurality of output drive couplings, each of the output drive couplings being drivingly coupled with a corresponding one of the drive motors, each of the output drive couplings being configured to drivingly couple with a corresponding input drive coupling of the surgical instrument;
   wherein a first drive motor of the plurality of drive motors is elongated between a first end, and a second end, the first drive motor includes a first magnetic flux shield at the first end and a second magnetic flux shield at the second end, and the first magnetic flux shield is spatially separated from the second magnetic flux shield so that a portion of the first drive motor unshielded from magnetic flux exists between the first magnetic flux shield and the second magnetic flux shield.

2. The robotic assembly of claim 1, wherein at least one of the plurality of drive motors includes a brushless component motor.

3. The robotic assembly of claim 2, wherein at least one of the plurality of drive motors includes a brushless component motor having a trapezoidal-commutation motor constant greater than or equal to 1.25 oz.-in/sqrt(Watt).

4. The robotic assembly of claim 1, wherein the magnetic flux shield includes a ring made of magnetically soft material containing at least one of iron, cobalt, or nickel.

5. The robotic assembly of claim 1, wherein each of the plurality of drive motors includes two magnetic flux shields that are disposed at opposite ends of the drive motor.

6. The robotic assembly of claim 5, wherein each of the magnetic flux shields comprises a ferrous ring.

7. The robotic assembly of claim 1, wherein two drive motors of the plurality of drive motors are separated by less than 5 mm.

8. The robotic assembly of claim 7, wherein two drive motors of the plurality of drive motors are separated by less than 2 mm.

9. The robotic assembly of claim 1, wherein:
   the plurality of drive motors includes five drive motors; and
   each of the five drive motors is separated from at least two of the other drive motors of the plurality of drive motors by less than 5 mm.

10. The robotic assembly of claim 9, wherein each of the five drive motors is separated from at least two of the other drive motors of the plurality of drive motors by less than 2 mm.

* * * * *